(12) United States Patent
Lewis et al.

(10) Patent No.: US 6,968,619 B2
(45) Date of Patent: Nov. 29, 2005

(54) METHOD FOR MANUFACTURING ENDODONTIC INSTRUMENTS

(75) Inventors: Paul Lewis, Midvale, UT (US); Barry L. Hobson, Grantsville, UT (US)

(73) Assignee: Ultradent Products, Inc., South Jordan, UT (US)

( * ) Notice: Subject to any disclaimer, the term of this patent is extended or adjusted under 35 U.S.C. 154(b) by 226 days.

(21) Appl. No.: 10/436,938

(22) Filed: May 13, 2003

(65) Prior Publication Data

US 2004/0229188 A1 Nov. 18, 2004

(51) Int. Cl.⁷ .......................... A61C 5/02; B23P 13/00
(52) U.S. Cl. .................... 29/896.1; 433/102; 216/91
(58) Field of Search ................... 29/896.1, 896.11; 433/102; 216/91; 72/299, 371; 140/149

(56) References Cited

U.S. PATENT DOCUMENTS

| | | | |
|---|---|---|---|
| 1,372,170 A | | 3/1921 | Judd |
| 2,173,218 A | | 9/1939 | Zoppi .............................. 76/24 |
| 2,434,286 A | * | 1/1948 | Pfann ........................... 205/664 |
| 2,724,918 A | * | 11/1955 | Triman .................... 156/345.15 |
| 3,803,014 A | | 4/1974 | Atkinson ...................... 204/206 |
| 3,823,514 A | | 7/1974 | Tsuchiya ....................... 51/281 |
| 3,869,373 A | | 3/1975 | Schacher et al. ............ 204/224 |
| 4,116,755 A | * | 9/1978 | Coggins et al. .............. 216/109 |
| 4,934,934 A | | 6/1990 | Arpaio, Jr. et al. .......... 433/102 |
| 5,382,319 A | | 1/1995 | Tumminaro, Jr. ............ 156/664 |
| 5,653,590 A | | 8/1997 | Heath et al. .................. 433/102 |
| 5,741,429 A | | 4/1998 | Donadio, III et al. ........... 216/8 |
| 5,762,541 A | | 6/1998 | Heath et al. .................... 451/48 |
| 5,762,811 A | | 6/1998 | Munoz .......................... 216/11 |
| 5,928,144 A | | 7/1999 | Real ............................. 600/378 |
| 5,941,760 A | * | 8/1999 | Heath et al. .................... 451/48 |
| 5,984,679 A | | 11/1999 | Farzin-Nia et al. .......... 433/102 |
| 6,086,773 A | | 7/2000 | Dufresne et al. ............... 216/8 |
| 6,315,558 B1 | | 11/2001 | Farzin-Nia et al. .......... 433/102 |
| 6,575,747 B1 | * | 6/2003 | Riitano et al. ............... 433/102 |

FOREIGN PATENT DOCUMENTS

| | | | |
|---|---|---|---|
| EP | 0118714 | 9/1984 | ........... A61B 17/32 |
| JP | 02002144154 | 5/2002 | ........... A61B 17/06 |

* cited by examiner

*Primary Examiner*—Eric Compton
(74) *Attorney, Agent, or Firm*—Workman Nydegger

(57) ABSTRACT

A method of manufacturing endodontic files involves a chemical milling process to yield endodontic files having a desired taper. The process involves the steps of (a) providing a metallic rod having a cutting portion with a polygonal cross section; (b) torsioning the rod so as to form helical cutting surfaces in the cutting portion of the metallic rod; and (c) chemically milling the cutting portion of the rod so as to taper the cutting portion. The rod may be formed of any desirable metallic material, for example stainless steel or a nickel-titanium alloy.

30 Claims, 9 Drawing Sheets

METHOD FOR MANUFACTURING ENDODONTIC INSTRUMENTS

BACKGROUND OF THE INVENTION

1. The Field of the Invention

The invention is in the field of endodontics and particularly to endodontic instruments for use in preparing root canals to receive a filling material such as gutta percha. More particularly, the invention is in the field of processes for manufacturing endodontic files.

2. The Relevant Technology

When a root canal of a living tooth becomes infected or abscessed, discomfort and, in many cases, severe pain can result. In the early days of dentistry the only solution was to pull the tooth. More recently, however, dental practitioners have learned to successfully remove the pulp material forming the nerve of the tooth that has become infected and, after careful preparation of the canal that contained the nerve material, refill the canal with an inert filling material, such as gutta percha, permitting a patient to retain the tooth.

In order to achieve a successful root canal restoration, the dental practitioner must carefully and, as completely as possible, remove the infected pulp material of the tooth to prevent continued or future infection of surrounding tissues. The removal process typically includes shaping of the root canal so that it can be effectively and successfully filled and sealed with an inert material to eliminate the possibility of further infection occurring within the cleaned and shaped root canal.

Cleaning and shaping the root canal in preparation to filling with a material such as gutta percha is achieved by the use of metal files that include cutting surfaces for removing tissue in the root canal. The cutting surfaces are typically formed by helical flutes formed in the file. One or more helical cutting surfaces may be provided, which may be axially spaced as desired.

Some existing endodontic instruments and manufacturing methods are described in U.S. Pat. Nos. 4,934,934, 5,653,590, and 5,762,541.

Since root canals are seldom straight, often having bends and twists, at least some endodontic files are advantageously flexible. Currently preferred materials of construction include stainless steel, and more recently, nickel-titanium (Ni—Ti) alloys. Such materials, especially Ni—Ti alloys, exhibit good flexibility, resilience and strength, and are not likely to fail during use. Flexibility and strength are important to avoid file breakage during the cleaning process.

Endodontic instruments may be designed to be manually manipulated or to be fitted to a powered handpiece that provides rotation of the file during its use. An endodontic instrument that is intended for hand use is typically provided with an enlarged diameter plastic handle attached to the proximal end of the instrument, configured for easy manipulation between the thumb and forefinger of the dental practitioner. An instrument intended for use with a powered handpiece has a stem at the instrument proximal end configured to be removably received within a chuck of the powered handpiece, by which the instrument may then be rotated as desired by a dental practitioner.

One current method of manufacturing existing endodontic files is by a grinding operation. In the grinding operation, a metallic (typically a titanium alloy) rod is advanced past a rotating grinding wheel at a relatively slow feed rate. The depth of cut may be varied along the length of the rod in order to produce a tapered endodontic file. Such a method is disclosed in U.S. Pat. No. 5,762,541.

Tapering and grinding the rod in this way requires complex and precise machining equipment with many moving parts to perform the grinding, rotating, and tapering of the rod. The method is quite complex and relatively expensive.

It would be an improvement in the art to provide an alternative method of manufacture capable of producing tapered endodontic instruments at a reasonable cost using machinery of reduced complexity.

BRIEF SUMMARY OF THE INVENTION

The present invention provides a method for manufacturing endodontic instruments. In one embodiment, the invention involves the steps of (a) providing a metallic rod having a cutting portion with a polygonal cross section; (b) torsioning the rod so as to form helical cutting surfaces in the cutting portion of the metallic rod; and (c) chemically milling the cutting portion of the rod so as to form a cutting portion having a desired taper.

The metallic rod may have any of various polygonal cross sections, such as triangular, square, or any of various regular or irregular shapes bounded by straight or curved sides. The cutting portion of the metallic rod is typically torsioned, which may be accomplished by holding one end of the cutting portion stationary while twisting the opposite end. Torsioning the rod causes the apices of the polygon to be twisted to form helical cutting surfaces along the cutting portion of the rod.

It will be appreciated that cutting surfaces can be formed in any manner known in the art. For example, a non-tapered file (or even a file having an initial taper) can be formed by any known method (e.g., grinding, cutting, particulate blasting, machining, laser micromachining, and the like) and then tapered using a chemical milling process to yield an endodontic instrument having a desired final taper.

Once an intermediate instrument having a cutting surface is formed, the cutting portion of the intermediate instrument is tapered by a chemical milling process. In one embodiment, the intermediate instrument is placed in a chemical bath. The bath composition may include hydrofluoric acid, nitric acid, water and a wetting agent. The longer the time that any specific portion of the file is in contact with the chemical milling solution, the greater will be the amount of metallic material stripped or removed from that portion. In one embodiment, at least the cutting portion of the metallic rod is submerged within the chemical milling composition and allowed to soak in the chemical milling solution. Allowing a soak time allows the chemical milling solution to remove the outer metal oxide layers of the cutting portion. Afterwards, the cutting portion is progressively withdrawn at a predetermined rate so as to result in a tapered cutting portion having a desired angle of taper. In another embodiment, no soak time is required, and the cutting portion may be progressively inserted and/or progressively withdrawn from the chemical milling solution, so as to result in a tapered cutting portion having a desired angle of taper.

Specific soak times (optional) and rates of insertion and/or withdrawal from the chemical milling composition depend on the chemical milling composition used, what type of material the intermediate file is formed from, the starting thickness of the rod, and the taper to be realized. When used, soak times preferably range from about 1 minute to about 1 hour, more preferably from about 3 minutes to about 30 minutes, and most preferably from about 5 minutes to about 20 minutes. Soaking removes the metal oxide layers that may otherwise interfere with the formation of a smooth taper.

Preferred rates of insertion and/or withdrawal range from about 0.1 mm per minute to about 6 mm per minute, more preferably from about 0.5 mm per minute to about 3 mm per minute and most preferably about 0.8 mm per minute to about 1.2 mm per minute.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

A detailed description of the invention endodontic instruments and manufacturing methods will now be provided, with specific reference to figures illustrating preferred embodiments of the invention. It will be appreciated that like structures will be provided with like reference designations. To provide context for interpreting the scope of the invention, certain terms used throughout the application will now be defined.

As used herein, the terms endodontic "instrument" and endodontic "instruments" refer to endodontic files and other instruments used in a root canal or other endodontic procedure. The terms "intermediate file" or "intermediate instruments" shall refer to metallic substrates before being chemically milled.

As used herein, the terms "polygon" and "polygonal" refer to a shape that is closed and bounded by straight or curved sides. Non-limiting examples include a triangle, a square, a rectangle, a pentagon, a spherical triangle, or any other of various regular or irregular shapes.

As used herein, the terms "chemical milling," "stripping" and "etching" refer to a procedure whereby a material is worked or shaped by exposure to a chemical bath. While exposed to the chemical bath, the shaping occurs as bits of material are "stripped" or "etched" off because of the chemical action of the bath.

As used herein, the term "soak time" refers to the amount of time that the metallic rod is exposed to the chemical milling composition of the chemical bath while in a stationary state. Soaking the metallic rod is optional and removes metal oxide layers that may otherwise interfere with the formation of a smooth taper.

I. Exemplary Endodontic Instruments

Figure 1:
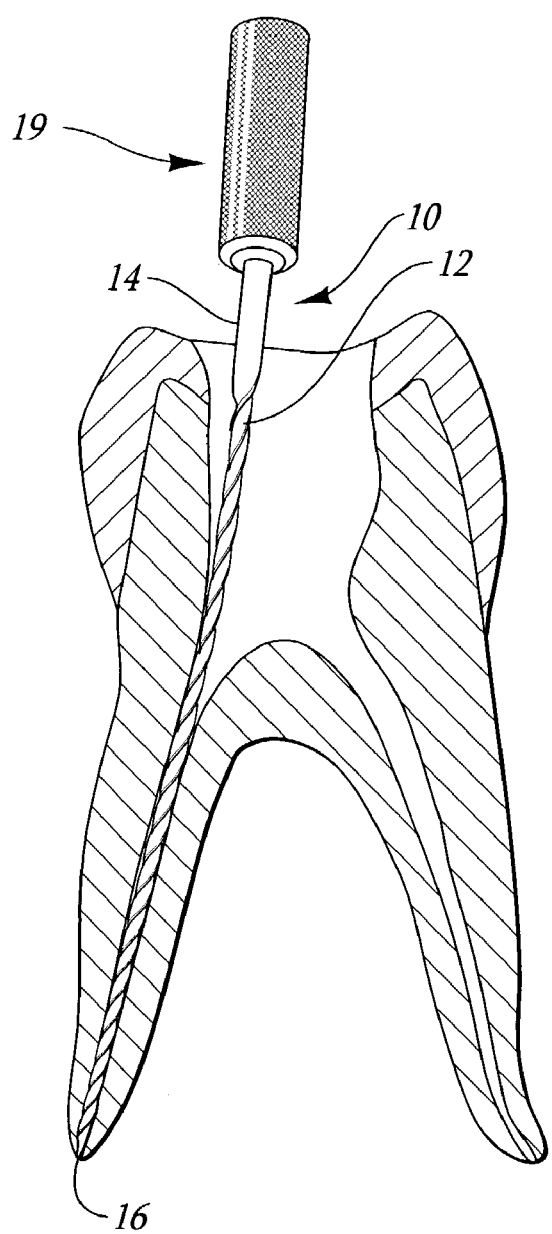
FIG. 1 is a cross sectional view of a tooth having two roots, with an endodontic instrument being positioned in one of the roots.
Figure 2:
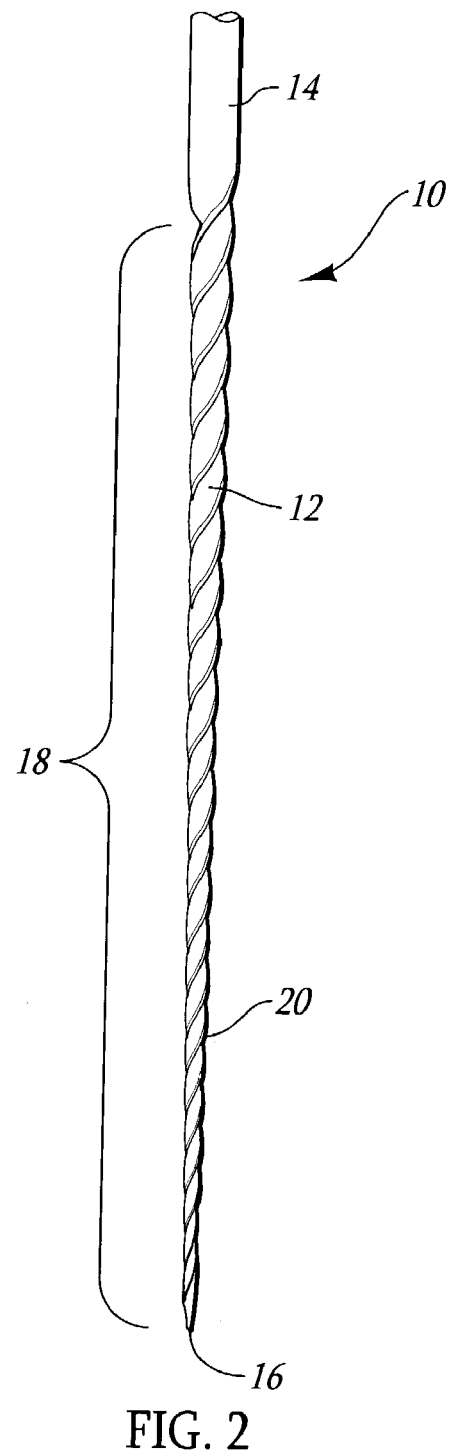
FIG. 2 is a perspective view of the cutting portion of an exemplary endodontic instrument.

Referring to FIGS. 1 and 2, an endodontic instrument 10 is illustrated which comprises a metallic rod 12 having a proximal end 14, and a distal end 16. At least a portion of the metallic rod 12 comprises a cutting portion 18 of the endodontic instrument, which is disposed between the proximal end 14 and the distal end 16. In this embodiment, the cutting portion 18 includes at least one helical cutting edge 20 that extends helically around metallic rod 12. A handle 19 may be provided adjacent the proximal end 14 of the metallic rod 12 in order to facilitate gripping of the endodontic instrument 10 by the user or a dental hand piece (e.g., a reciprocating hand piece).

The cutting portion 18 is preferably tapered between the proximal end 14 and the distal end 16, with decreasing diameter or width toward the distal end 16. The taper may be continuous or incremental (i.e. stair stepped). The taper may be any amount desired, but is preferably between about 0.02 mm/mm and about 0.06 mm/mm. The specific taper of any instrument will depend on the intended use and dental practitioner preference. For example, a taper of 0.0225 mm/mm may be preferred when preparing a root canal that is to receive a gutta percha cone having a taper of about 0.02 mm/mm.

The cutting portion 18 may have a length of about 2 mm up to the full length of the rod 12, which may be as much as about 30 mm or more. In the illustrated embodiment, the cutting portion 18 has a length sufficient to extend substantially the full depth of a tooth root canal as illustrated in FIG. 1. It will be appreciated, however, that the cutting portion may terminate before reaching the tip 16, as in a coronal file, or comprise a small length near the tip 16 as in an apical file.

Figure 3A:
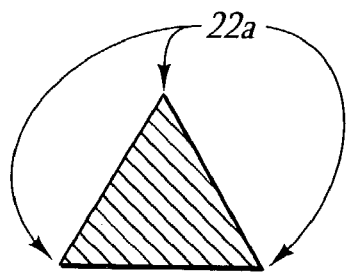
FIGS. 3A–3G illustrate several different polygonal transverse cross sections through several exemplary endodontic instruments manufactured according to the method of the present invention.

The cross sectional configuration of the cutting portion 18 of the instrument illustrated in FIGS. 1 and 2 is triangular and is composed of three linear sides, as best seen in FIG. 3A. The apices 22a of the triangle form cutting edges 20. The cutting portion 18 may be of any polygonal cross section such that when the rod is torsioned, cutting edges 20 are formed.

Figure 3B:
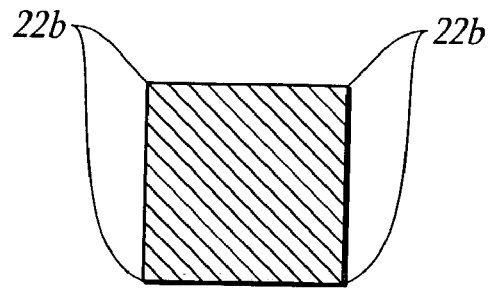
Figure 3C:
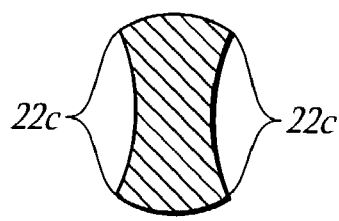

Several non-limiting examples of suitable polygonal cross sections are illustrated in FIGS. 3A–3G. FIG. 3A illustrates a triangular cross section in which apices 22a form three cutting edges 20. FIG. 3B illustrates a square cross section in which line intersections 22b form four cutting edges. FIG. 3C illustrates a cross section bounded by four curved sides, two of which are concave and two of which are convex. The intersections 22c between the convex and concave sides form four cutting edges.

Figure 3D:
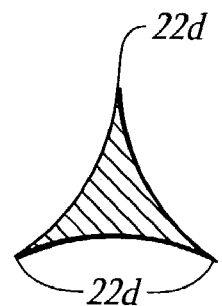
Figure 3E:
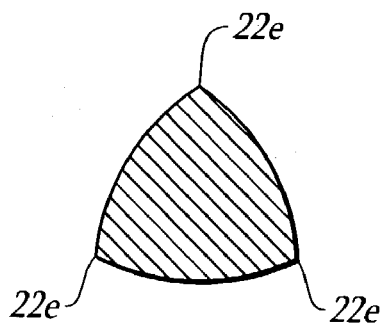

FIGS. 3D and 3E illustrate alternative spherical triangular cross sections, with the triangle cross section of FIG. 3D having concave surfaces between the apices 22d of the triangle and with the triangle cross section of FIG. 3E having convex surfaces between apices 22e of the triangle.

Figure 3F:
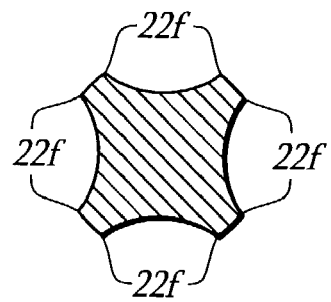
Figure 3G:
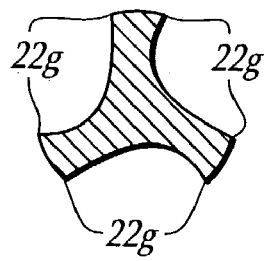

FIG. 3F illustrates a cross section bounded by a combination of four concavely curved sides separated by four straight sides. The intersection 22f between the straight and curved sides form eight cutting edges. FIG. 3G illustrates a cross section of an irregular polygon bounded by three concavely curved sides separated by three convexly curved sides. The intersections 22g between the six curved sides yield six cutting surfaces.

When torsioned, the apices or edges 22a–g of the various cross sections form helical cutting edges 20.

II. Method of Manufacture

FIGS. 4 and 5A–5E illustrate an exemplary method of manufacturing endodontic instruments according to the present invention. As will be further described below, the method involves a unique process which has been found to efficiently produce endodontic instruments of the type described, from a metallic wire. The metallic wire may be formed of any suitable metallic material, for example stainless steel, a nickel-titanium alloy (Ni—Ti), nickel-titanium-chromium alloy, a nickel-titanium-copper alloy, a nickel-titanium-niobium alloy, or any other superelastic metallic material. Although any suitable metallic material may be used, nickel-titanium alloys are preferred because they are strong yet flexible and resilient. The Ni—Ti alloy preferably has a titanium content in a range of about 20% to about 80%, more preferably in a range of about 30% to about 70%, and most preferably in a range of about 40% to about 60%. In one embodiment, the balance of the alloy may comprise nickel and small amounts of other ingredients which do not adversely affect the suitability of the material for use as an endodontic instrument.

The wire from which the endodontic instrument is to be manufactured may be supplied already drawn in a selected polygonal cross sectional shape. Alternatively, the wire may be supplied in a circular cross section and then shaped to the desired cross section by processes known to those of skill in the art. With regard to wire thickness, endodontic instruments are sized in accordance with established standards, which range from a thickness at the distal end 16 of 1.4 mm (size 140) to a thickness at the distal end 16 of 0.06 mm (size 06).

Figure 4:
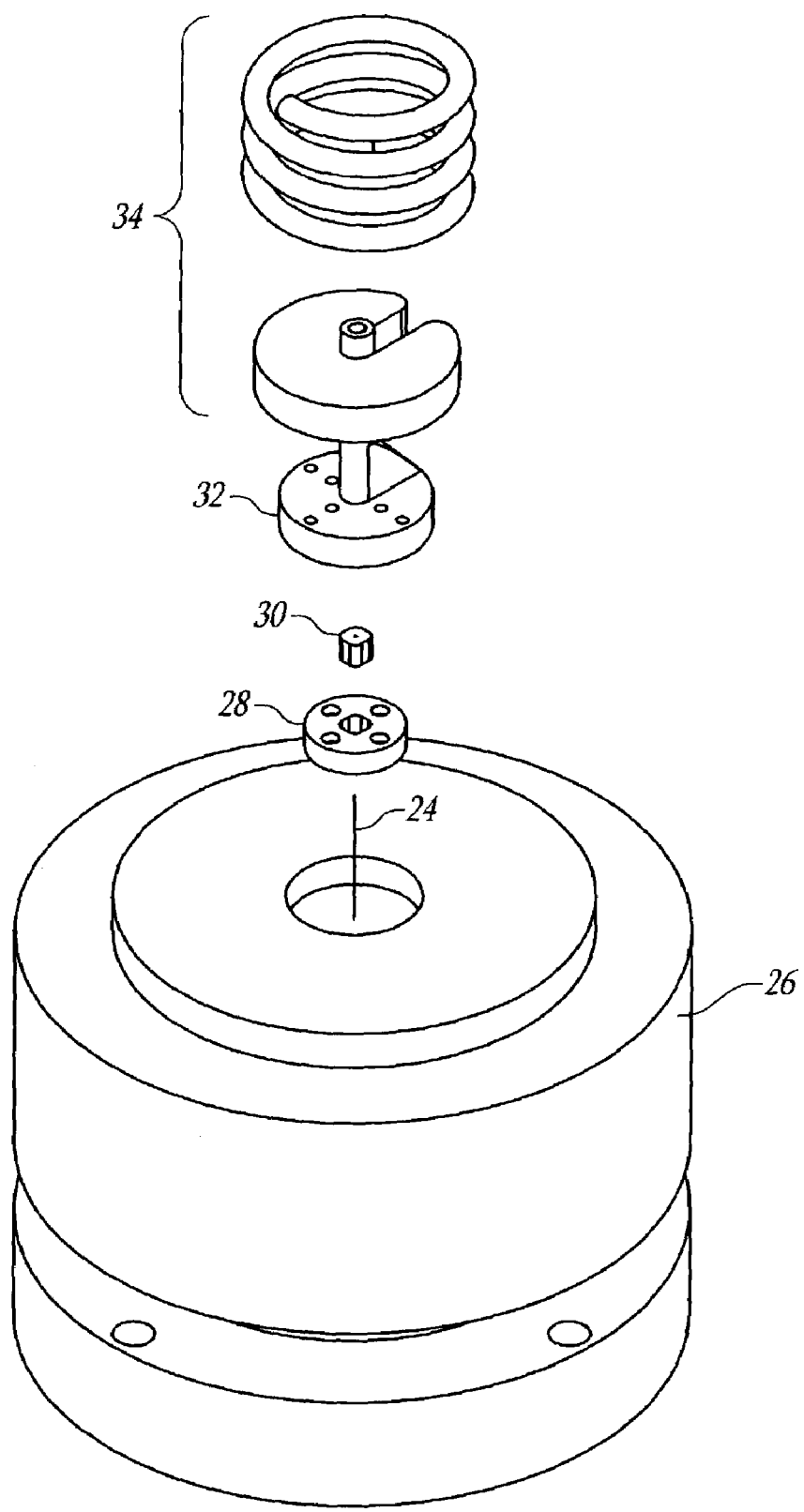
FIG. 4 is an exploded view of an apparatus for torsioning metallic rods for manufacturing endodontic instruments according to the present invention.

FIG. 4 depicts an exemplary apparatus (in exploded view) for performing the first steps of an exemplary method of manufacture. The exemplary apparatus includes a collet 26, housing cap 28, insert 30, insert housing 32, and coil assembly 34. The continuous wire is first cut to a desired length. The wire length 24 is positioned to extend out of collet 26, which may be of well known construction. Wire length 24 extends out collet 26 and into insert 30, which is nearly surrounded by housing cap 28. In order to receive wire 24, insert 30 includes a passage through its center having the same cross section shape as wire 24. The passage is slightly larger than wire 24 so as to allow clearance for the wire 24 to be received within insert 30. The ends of the passage may be flared so as to facilitate inserting the wire 24 through the passage.

Insert 30 is formed of a hard material, preferably a ceramic such as cermet. The insert 30 and housing cap 28 are received within insert housing 32. Coil assembly 34 (for heating) surrounds the insert housing and insert. The wire 24 is heated, and then torsioned. Torsion is accomplished by turning and retracting the collet 26.

The wire 24 may be heated by any known method prior to torsioning. Examples of suitable heating methods include electrical resistive heating, convection heating, direct heating by a torch, or RF high frequency induction heating. RF high frequency induction heating is a preferred heating method. In RF high frequency induction heating, the wire 24 is heated while positioned through coil assembly 34 into which an electrical current is fed. The electrical current and coil assembly 34 create a heating field that may be focused on the wire 24 as it is positioned through the coil assembly 34. Heating wire 24 makes it easier to subsequently torsion the wire.

In order to avoid oxidation of the metal wire 24 while heating, when possible, the heating is preferably performed in an inert environment, such as under a noble gas environment. Examples of inert gases that may be used include, but are not limited to, helium, argon and even nitrogen in those cases where the heated metal does not adversely react with nitrogen to form a brittle product. Because allows of titanium can react with nitrogen to form titanium nitride, which is brittle, it may not be advantageous to use nitrogen gas when manufacturing an endodontic file from titanium alloys. Nitrogen works well with other metals, such as stainless steel.

Insert 30 and collet 26 function together to torsion wire 24. While both ends of the wire 24 are gripped, collet 26 turns, which twists the wire 24 about its longitudinal axis. This causes the apices or intersections 22 of the polygonal cross section of the wire 24 to form helical cutting edges 20 as described above with respect to FIGS. 1 and 2. Collet 26 is retracted either during or after turning, removing wire 24 from insert 30.

Once a length of wire 24 has been cut and torsioned to form a metallic rod 12, the rod is ready to be tapered. Although the current example tapers the rod after torsioning, the order is not critical, and the torsioning process could be performed after tapering. In either case, the cutting portion 18 is tapered by chemically milling at least the cutting portion 18 of the metallic rod 12. The cutting portion 18 of rod 12 is chemically milled by placing the cutting portion 18 in a chemical milling composition. The composition may contain an acid, water, and a wetting agent. Suitable acids include hydrofluoric acid and nitric acid. One currently preferred composition includes about 10% hydrofluoric acid, about 20% nitric acid, about 0.8% Dapco 6001, a wetting agent, and the balance water. Percentages are given as percent by volume.

It is preferable to maintain the chemical milling solution at a temperature between about 15° and about 105° C., more preferably about 25° and about 90° C., and most preferably about 35° and about 65° C.

In addition, it is preferable to stir the chemical milling solution. Suitable stirring rates include about 1 to 1200 RPM.

The cutting portion 18 of each rod 12 is tapered by progressively inserting and/or withdrawing the cutting portion 18 from the chemical milling composition 36. FIGS. 5A–5E illustrate tapering by progressively withdrawing the cutting portion 18. The rate at which the rod 12 is inserted and/or withdrawn from the composition 36 will depend on the chemical milling composition 36 used, what type of material the rod 12 is formed of, the starting thickness of the rod 12, and the taper to be realized. Slower rates of insertion and/or withdrawal result in longer treatment times, which generally result in greater tapering of the cutting portion 18.

In one embodiment, it may be desirable to soak at least said cutting portion in said chemical milling composition for a predetermined soak time prior to withdrawal from the chemical milling composition. When used, preferably soak times are from between about 1 minute and about 60 minutes, more preferably 3 minutes to about 30 minutes, and most preferably about 5 minutes to about 20 minutes. Soaking strips off the outer metal oxide layers, which may result in a smoother taper.

The amount of metallic material stripped away by the milling composition is proportional to the treatment time of any specific portion of the metallic rod. In order to strip or etch more metal from the distal end 16 of the endodontic file 10, the distal end 16 of the endodontic instrument 10 will be submerged longer in the composition 36 than the rest of the cutting portion 18 of rod 12. The cutting portion 18 of rod 12 is progressively inserted and/or withdrawn from the composition 36 at a predetermined rate, resulting in a metallic rod with a tapered cutting portion 18.

The metallic rod 12 may be inserted and/or withdrawn at any desired rate, although it is preferable to insert and/or withdraw the rod 12 at a rate of between about 0.1 mm per minute to about 6 mm per minute, more preferably about 0.5 mm per minute to about 3 mm per minute and most preferably about 0.8 mm per minute to about 1.2 mm per minute. The specific rate of insertion and/or withdrawal depends on the actual chemical milling composition 36 used, what type of material the rod 12 is formed of, the starting thickness of the rod 12, and the taper to be realized. One of ordinary skill will be able to select a rate that will yield a desired taper for a given metallic rod.

The metallic rod 12 is preferably inserted and/or withdrawn continuously from the chemical milling composition 36 so as to form a smooth taper, although the rod 12 could alternately be inserted and/or withdrawn incrementally from the chemical milling composition. Incremental insertion and/or withdrawal results in a stepped taper rather than a smooth taper, which may be desirable in some applications.

Figure 5A:
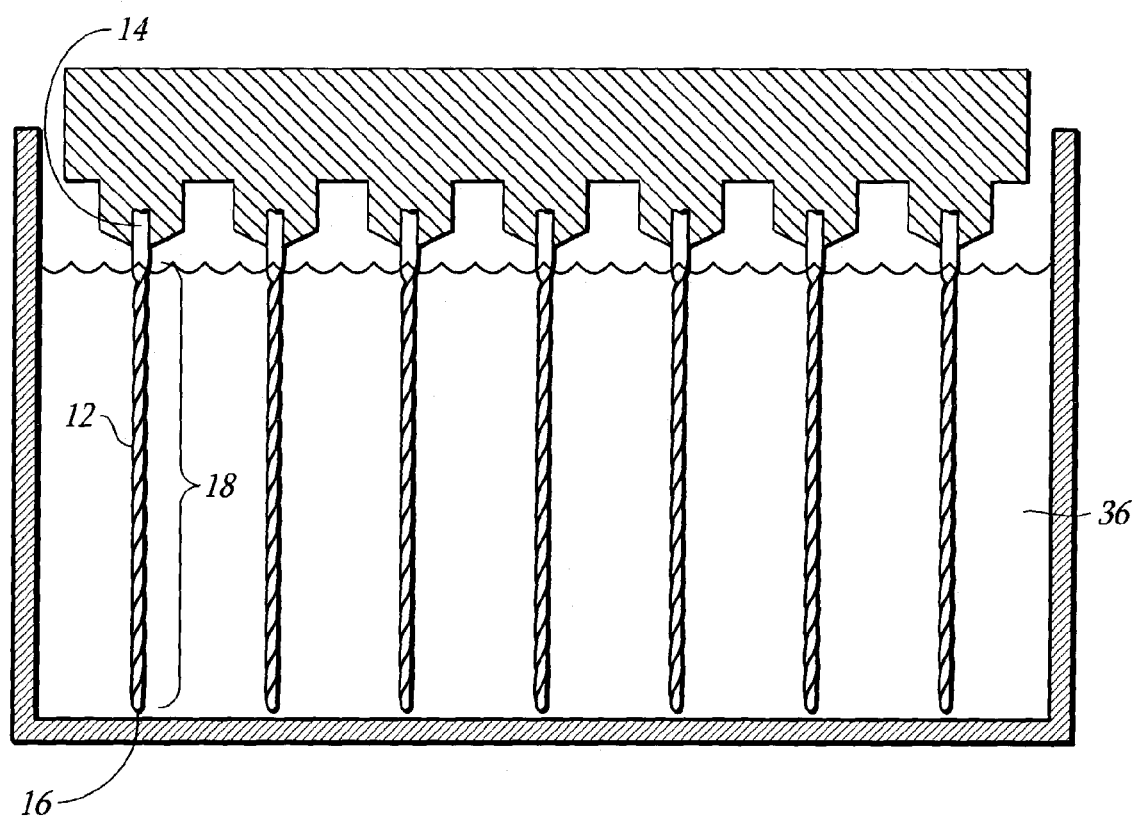
FIGS. 5A–5E depict exemplary torsioned metallic rods being chemically milled to taper the cutting portions of the metallic rods.
Figure 5B:
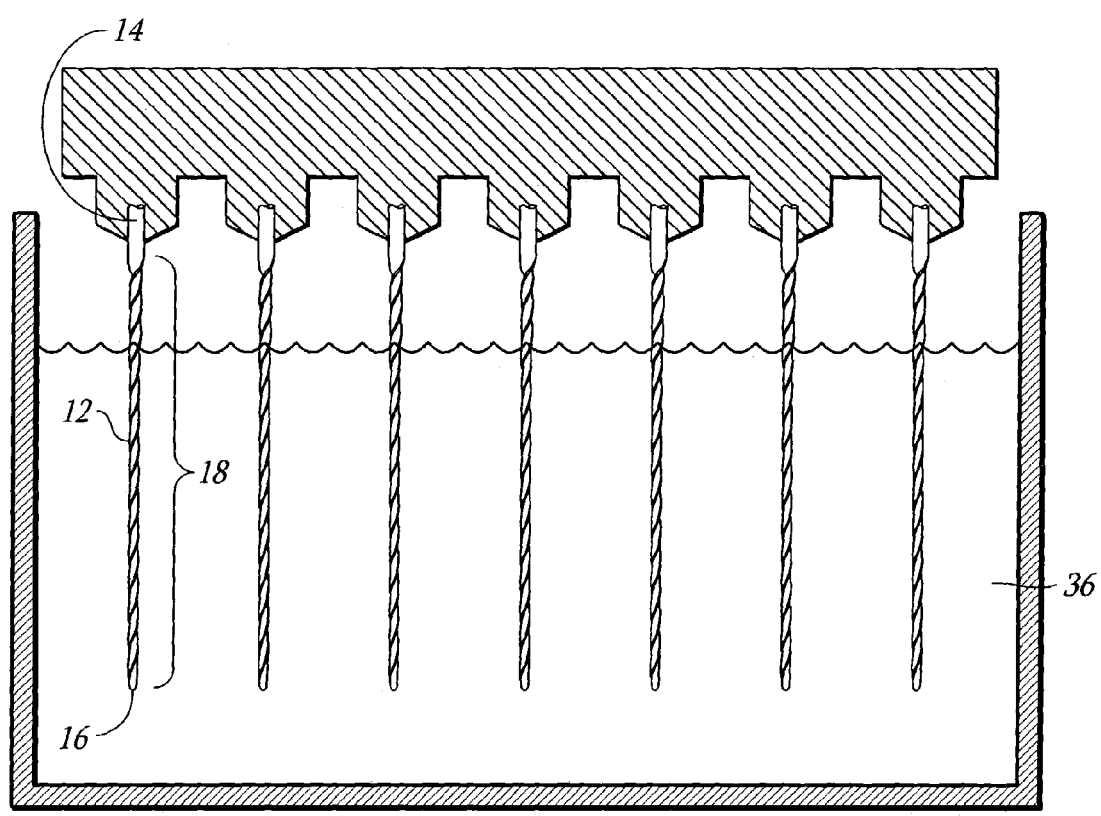
Figure 5C:
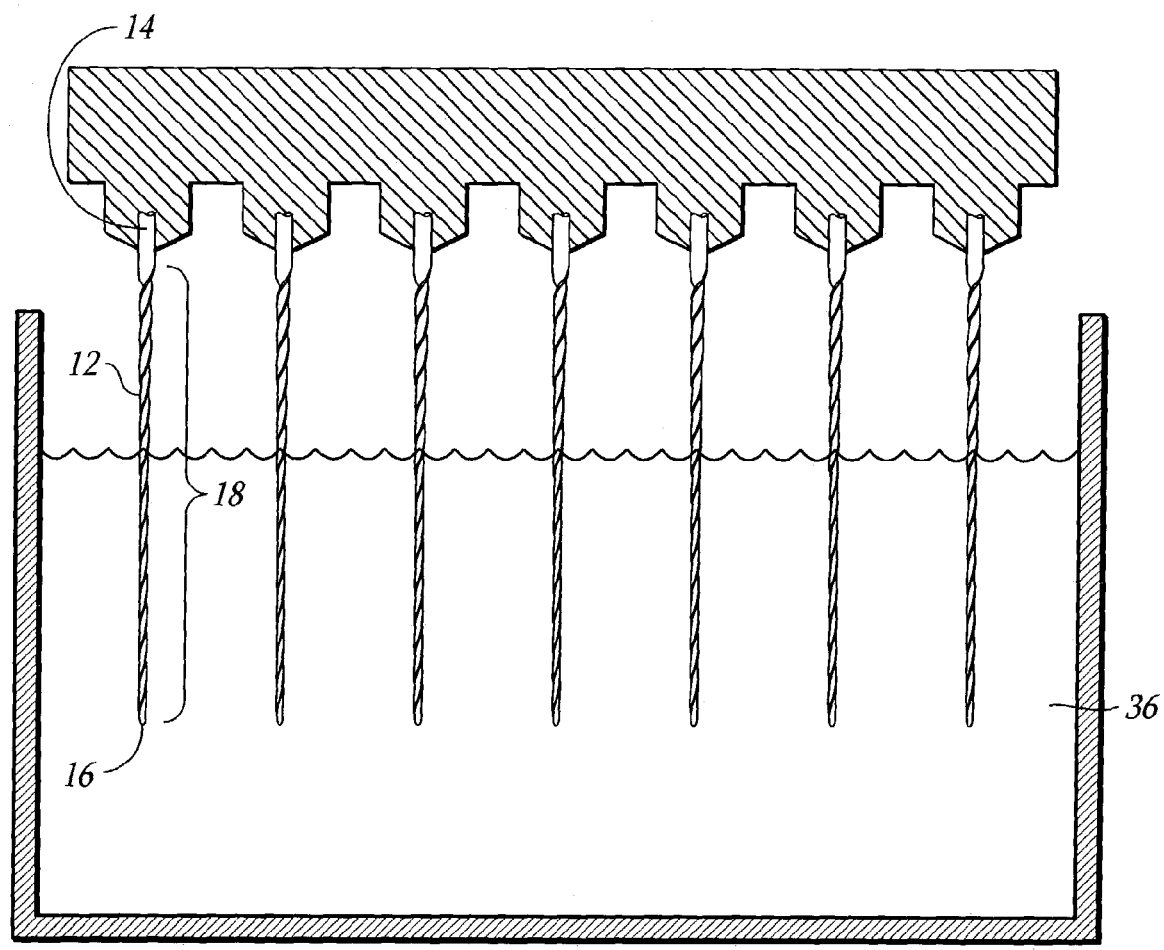
Figure 5D:
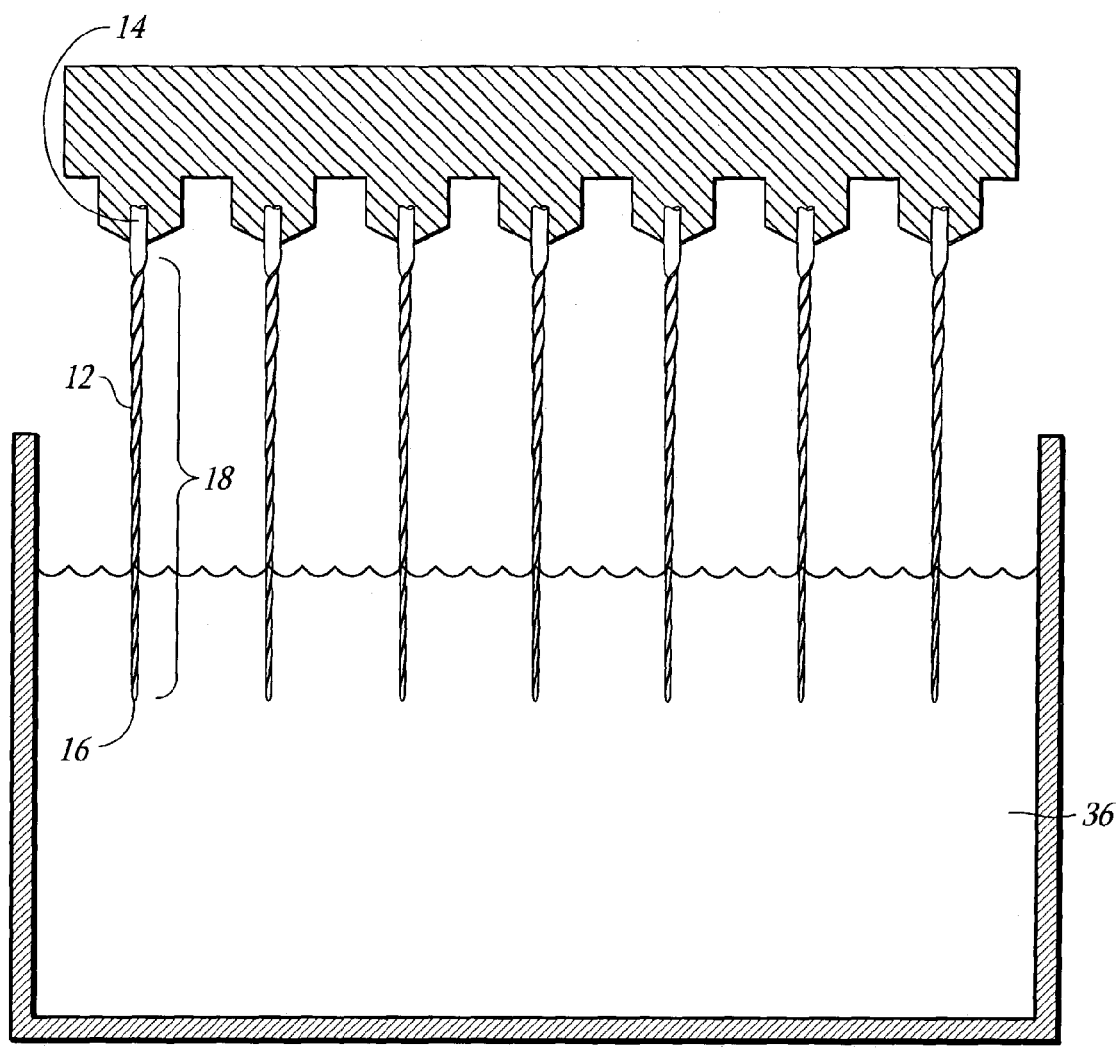
Figure 5E:
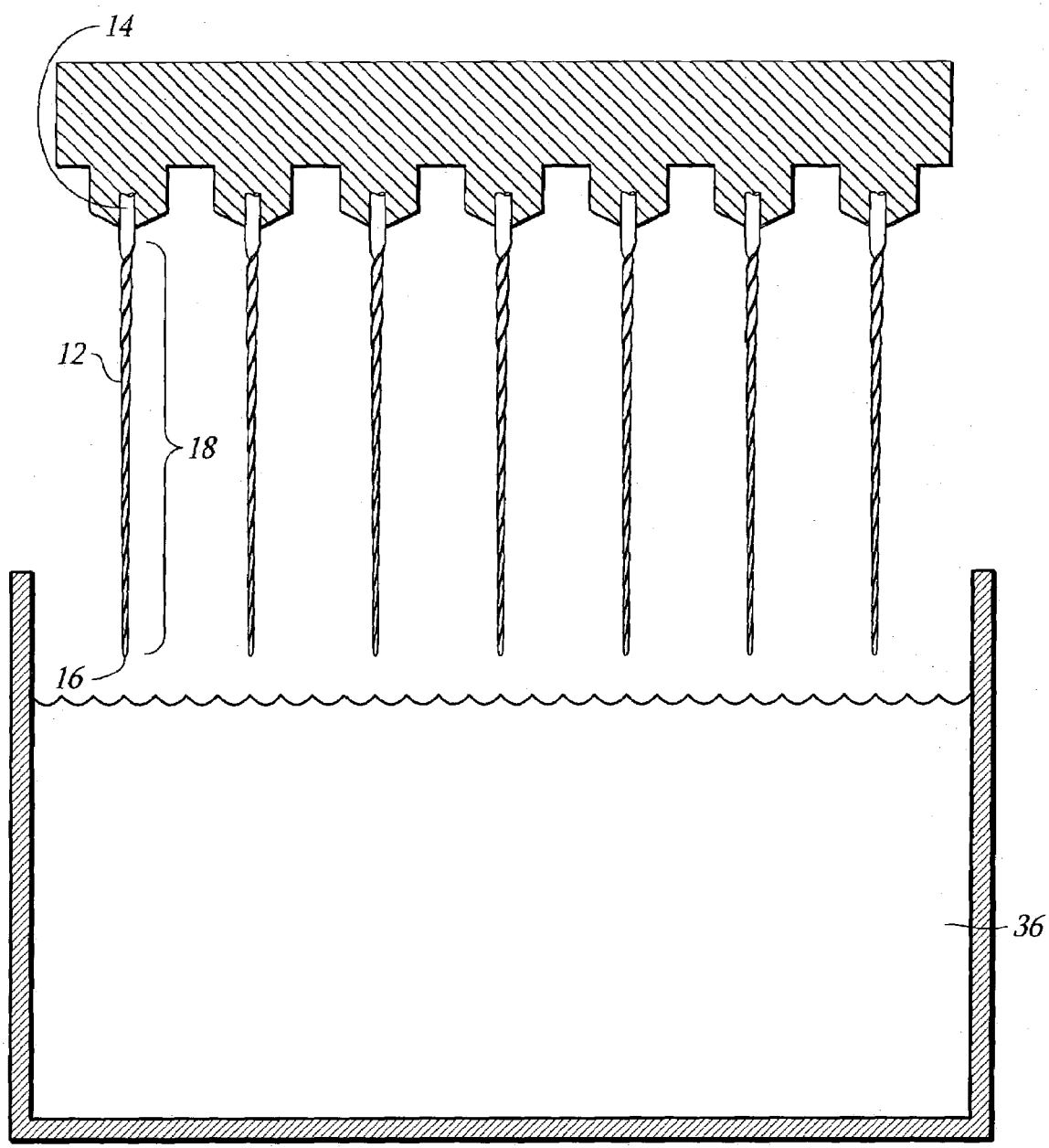

FIGS. 5A–5E illustrate different stages during the chemical milling process where the rod 12 is progressively withdrawn from the milling composition 36. FIG. 5A illustrates a state at the beginning of the chemical milling process where the entire cutting portion 18 of each metallic rod 12 is submerged in the composition 36. FIG. 5B illustrates an intermediate stage during the chemical milling process where the cutting portion 18 of rod 12 has been partially withdrawn from milling composition 36. FIG. 5C illustrates a more advanced intermediate stage where cutting portion 18 has been further withdrawn, while FIG. 5D illustrates a yet more advanced intermediate stage where cutting portion 18 has been almost completely withdrawn. FIG. 5E illustrates a stage where the cutting portion 18 has been completely withdrawn from milling composition 36.

Figure 6A:
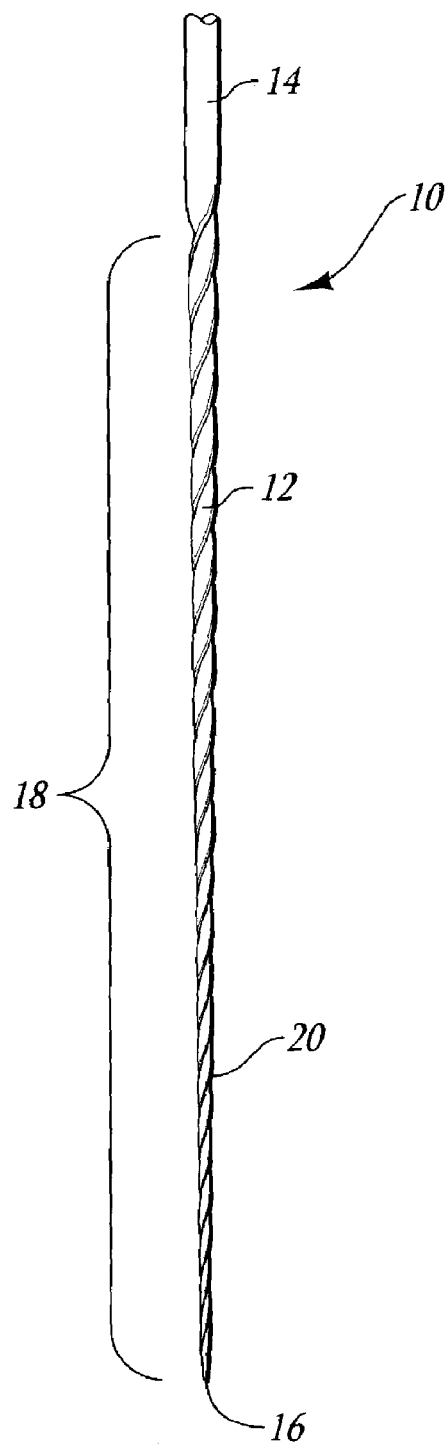
FIGS. 6A and 6B depict exemplary tapered metallic rods.
Figure 6B:
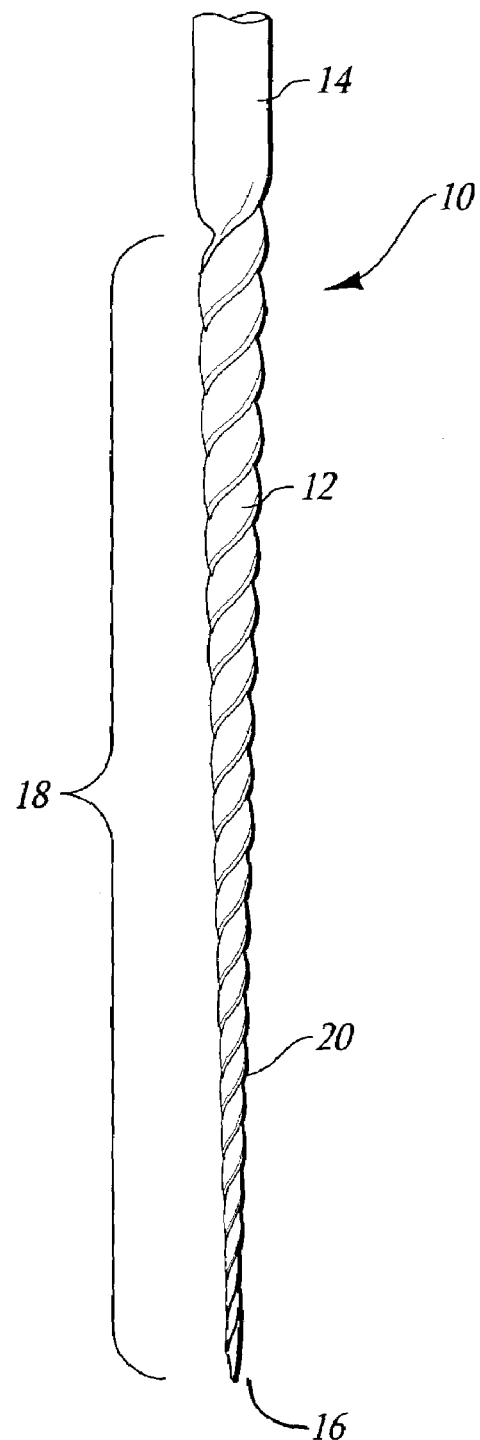

FIGS. 6A–6B illustrate exemplary endodontic instruments 10 having continuous tapered cutting portions 18. The instrument illustrated in FIG. 6A includes a taper of about 0.02 mm/mm while that illustrated in FIG. 6B includes a taper of about 0.06 mm/mm.

After chemical milling, the rod 12 is then further processed in a conventional manner to form the completed instrument as illustrated for example in FIG. 1 (e.g. fitting a handle or stem 19 to proximal end 14, optionally surface finishing the rod 12, etc). The process as described and claimed has been found to produce inexpensive high quality endodontic instruments. In addition, with at least some polygonal cross sections, tapering by chemical milling has been found to result in cutting surfaces which sharpen as they are chemically milled. The process is suitable for commercial application to manufacture as few or as many instruments at a time as desired, and does not require the complex mechanical milling machinery required by existing manufacturing methods.

It will be appreciated that the cutting surfaces or edges of the endodontic instruments may be formed by other means known in the art instead of torsioning. For example, they may be formed by cutting, grinding, grit blasting, machining, laser micromachining, and the like.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A method of manufacturing an endodontic instrument for use in performing an endodontic procedure, comprising:
   (a) forming an intermediate instrument having a cutting portion by at least one of (i) torsioning a metallic rod having a polygonal cross section or (ii) cutting, grinding, laser micromachining, machining, or grit blasting a metallic rod; and
   (b) chemically milling at least said cutting portion of said intermediate instrument so as to yield an endodontic instrument having a desired taper.

2. The method as recited in claim 1, wherein at least a portion of said cutting portion is formed by (c) torsioning a metallic rod having a polygonal cross section so as to form helical cutting edges in said cutting portion.

3. The method as recited in claim 2, wherein said polygonal cross section is at least one of a square, a triangle, a polygon having straight surfaces, a polygon having concave surfaces, or a polygon having convex surfaces.

4. The method as recited in claim 2, wherein said metallic rod is heated prior to and/or during torsioning.

5. The method as recited in claim 4, wherein said metallic rod is heated by RF high frequency induction heating.

6. The method as recited in claim 4, wherein said heating is performed in an inert environment.

7. The method as recited in claim 6, wherein said inert environment comprises at least one noble gas.

8. The method as recited in claim 1, wherein at least a portion of said cutting portion is formed by at least one of cutting, grinding, laser micromachining, machining, or grit blasting.

9. The method as recited in claim 1, wherein said chemical milling is performed by progressively inserting and/or withdrawing said cutting portion from a chemical milling composition at a predetermined rate.

10. The method as recited in claim 9, wherein said chemical milling composition is acidic.

11. The method as recited in claim 10, wherein said chemical milling composition comprises one or more of hydrofluoric acid, nitric acid, water, and a wetting agent.

12. The method as recited in claim 9, wherein said chemical milling composition is maintained at a temperature between about 15° and about 105° C.

13. The method as recited in claim 9, wherein said chemical milling composition is maintained at a temperature between about 25° and about 90° C.

14. The method as recited in claim 9, wherein said chemical milling composition is maintained at a temperature between about 35° and about 65° C.

15. The method as recited in claim 9, further comprising soaking at least said cutting portion in said chemical milling composition for a predetermined soak time of between about 1 minute and about 60 minutes.

16. The method as recited in claim 15, wherein said soak time is between about 3 minutes and about 30 minutes.

17. The method as recited in claim 15, wherein said soak time is between about 5 minutes and about 20 minutes.

18. The method as recited in claim 9, wherein said cutting portion of said rod is inserted and/or withdrawn from said chemical milling composition at a rate of between about 0.1 mm per minute and about 6 mm per minute.

19. The method as recited in claim 9, wherein said cutting portion of said rod is inserted and/or withdrawn from said chemical milling composition at a rate of between about 0.5 mm per minute and about 3 mm per minute.

20. The method as recited in claim 9, wherein said cutting portion of said rod is inserted and/or withdrawn from said chemical milling composition at a rate of between about 0.8 mm per minute and about 1.2 mm per minute.

21. The method as recited in claim 1, wherein said chemically milling produces a cutting portion taper of between about 0.02 mm/mm and about 0.06 mm/mm.

22. The method as recited in claim 21, wherein said chemically milling produces a cutting portion taper of about 0.0225 mm/mm.

23. The method as recited in claim 1, wherein said chemically milling sharpens the cutting surfaces of said cutting portion as said cutting portion is chemically milled.

24. The method as recited in claim 1, wherein said chemically milling comprises chemically milling a plurality of intermediate instruments simultaneously.

25. A method of manufacturing an endodontic instrument for use in performing an endodontic procedure, comprising:
   (a) torsioning a metallic rod having a polygonal cross section so as to form an intermediate instrument having a cutting portion with helical cutting edges in said cutting portion; and
   (b) chemically milling at least said cutting portion of said intermediate instrument so as to yield an endodontic instrument having a desired taper.

26. The method as recited in claim 25, wherein said chemically milling sharpens said helical cutting edges as said cutting portion is chemically milled.

27. The method as recited in claim 25, further comprising subjecting said metallic rod to at least one of cutting, grinding, laser micromachining, machining, or grit blasting.

28. A method of manufacturing an endodontic instrument for use in performing an endodontic procedure, comprising:
   (a) forming an intermediate instrument having a cutting portion from a metallic rod, at least said cutting portion formed by at least one of cutting, grinding, laser micromachining, machining, or grit blasting; and
   (b) chemically milling at least said cutting portion of said intermediate instrument so as to yield an endodontic instrument having a desired taper.

29. The method as recited in claim 28, wherein said chemically milling sharpens cutting edges of said cutting portion as said cutting portion is chemically milled.

30. The method as recited in claim 28, further comprising torsioning said metallic rod to yield helical cutting edges.

* * * * *